US008579925B2

(12) United States Patent
Staggs

(10) Patent No.: US 8,579,925 B2
(45) Date of Patent: Nov. 12, 2013

(54) MEDICAL CLAMP

(75) Inventor: Stephen M. Staggs, Nashville, TN (US)

(73) Assignee: Symmetry Medical, Inc., Warsaw, IN (US)

(*) Notice: Subject to any disclaimer, the term of this patent is extended or adjusted under 35 U.S.C. 154(b) by 59 days.

(21) Appl. No.: 13/177,872

(22) Filed: Jul. 7, 2011

(65) Prior Publication Data

US 2012/0010654 A1 Jan. 12, 2012

Related U.S. Application Data

(60) Provisional application No. 61/361,994, filed on Jul. 7, 2010.

(51) Int. Cl.
*A61B 17/08* (2006.01)
(52) U.S. Cl.
USPC .......................................... 606/157; 269/271
(58) Field of Classification Search
USPC ......... 606/119, 120, 151, 157, 201, 203–208, 606/213, 215, 216; 269/86, 216, 257, 271
See application file for complete search history.

(56) References Cited

U.S. PATENT DOCUMENTS

| 3,364,919 | A | | 1/1968 | Hunnicutt |
| 4,223,673 | A | * | 9/1980 | Harris ........................... 604/115 |
| 6,099,539 | A | * | 8/2000 | Howell et al. ................. 606/151 |
| 6,315,780 | B1 | * | 11/2001 | Lalonde ....................... 606/86 R |
| 2002/0111537 | A1 | | 8/2002 | Taylor et al. |
| 2002/0116025 | A1 | | 8/2002 | Haab |
| 2007/0142860 | A1 | | 6/2007 | Kotmel et al. |

OTHER PUBLICATIONS

European Search Report dated Oct. 14, 2011 for EP 11 00 5533 (7 pages).
Vaman B. Ghodake, Suchitra N. Pandit, Shashikant M. Umbardand, "Role of Modified B-lynch Suture in Modern Day Management of Atonic Postpartum Haemorrhage"; Bombay Hospital Journal, vol. 50, No. 2, 2008, pp. 205-211.
David Lagrew MD, Andrew Hull MD, "Uterine Hemostatic Sutures"; Saddleback Memorial Medical Center, University of California, San Diego; programs funded by grants from the California Department of Public Health, Center for Family Health, Maternal Child and Adolescent Health Division; no date of publication on document (2 pages).
Koh E, Devendra K, Tan L K, "B-Lynch suture for the treatment of uterine atony"; Singapore Med J 2009; 50(7): 693-607.
David Lagrew MD, Andrew Hull MD, "Uterine Hemostatic Sutures"; Saddleback Memorial Medical Center, University of California, San Diego; CMQCC (California Maternal Quality Care Collaborative); CMQCC obstetric hemorrhage toolkit, obstetric care guidelines and compendium of best practices, reviewed by CADPH-MCAH: Dec. 22, 2009 (understood to be California Department of Public Health—Maternal, Child and Adolescent Health); printed from internet on Jan. 2, 2012 (3 pages).

(Continued)

*Primary Examiner* — Dianne Dornbusch
*Assistant Examiner* — Robert Lynch
(74) *Attorney, Agent, or Firm* — Taylor IP, P.C.

(57) ABSTRACT

A medical clamp includes a lower arm assembly, an upper arm assembly, and a belt. The upper arm assembly is pivotally connected to the lower arm assembly. The lower arm assembly and the upper arm assembly are configured for clamping relative to one another. The belt is connected to the lower arm assembly and the upper arm assembly and is configured for forming a loop therebetween.

4 Claims, 9 Drawing Sheets

(56) References Cited

OTHER PUBLICATIONS

Image of Buxton Uterine Clamp by Thomas Medical of Indianapolis, Indiana; printed from internet on Jan. 3, 2012 from http://www.thomasmedical.com/buxtonuterineclamp.aspx. (1 page).

Image of Collin Uterine Clamp by Thomas Medical of Indianapolis, Indiana; printed from internet on Jan. 3, 2012 from http://www.thomasmedical.com/collinuterineclamp.aspx. (1 page).

Image of Green Armytage Uterine Clamp by surgicaltools.com of Bedford, Virginia; printed from internet on Jan. 3, 2012 from http://www.surgicaltools.com/product.htm?id=3bg8n9p8. (1 page).

Download of 3 page from the internet. Pages are entitled "Uterine Clamp to Manage Blood Loss During Cesarean Section", by Katherine W. Kent, M.D. Pages are available at http://uvapf.org/live_data/live_site_page.php?page_id=17&technology_id=44. Pages are published by University of Virginia Patent Foundation and were available on the Internet at least as of Aug. 3, 2011. One of the pages (labeled as p. 2 of 2) shows a copyright of 2010 by University of Virginia Patent Foundation.

Wikipedia article entitled, "Lower segment Caesarean section". Article was downloaded from the Internet on Jul. 2, 2011 at http://en.wikipedia.org/wiki/Lower_uterine_segment_section (1 page).

Wikipedia article entitled, "Placenta". Article was downloaded from the internet on Jul. 2, 2011 at http://en.wikipedia.org/wiki/Placenta (8 pages).

Document published by World Health Organization entitled, "WHO guidelines for the management of postpartum haemorrhage and retained placenta". Document was published in 2009 apparently in Geneva Switzerland. Document was prepared by Dr. A. Metin Gülmezoglu, Dr. João Paulo Souza, Dr. Doris Chou, Dr. Matthews Mathai, Dr. Suzanne Hill, Dr. Edgardo Abalos. (62 pages).

\* cited by examiner

MEDICAL CLAMP

CROSS REFERENCE TO RELATED APPLICATIONS

This is a non-provisional application based upon U.S. provisional patent application Ser. No. 61/361,994, entitled "MEDICAL CLAMP", filed Jul. 7, 2010, which is incorporated herein by reference.

BACKGROUND OF THE INVENTION

1. Field of the Invention

The present invention relates to medical instruments, and, more particularly, to medical clamps.

2. Description of the Related Art

Control of postpartum hemorrhage is as old as humanity but it is still a major health problem in first, second, and third world countries. Postpartum hemorrhage is the greatest cause, and thus the most significant cause, of maternal morbidity and mortality in the world. Postpartum hemorrhage is one of the most common and devastating complications of childbirth. Uterine Atony is the most common cause of this hemorrhage (75-85%). Currently, uterotonic drugs such as pitocin, methergine, and other drugs are used in an attempt to encourage the uterus to contract and to slow the bleeding. If the drugs are not effective, then a cascade of events are put into action to try to save the life and hopefully the reproductive capabilities of the parturient. A multidisciplinary approach to control hemorrhage and to maintain the parturient's blood volume and blood pressure is instituted.

What is needed in the art is a way to more effectively control postpartum hemorrhage.

SUMMARY OF THE INVENTION

The present invention provides a way to more effectively control postpartum hemorrhage.

The invention in one form is directed to a medical clamp, including: a lower arm assembly; an upper arm assembly pivotally connected to the lower arm assembly, the lower arm assembly and the upper arm assembly being configured for clamping relative to one another; and a belt connected to the lower arm assembly and the upper arm assembly and configured for forming a loop therebetween.

The invention in another form is directed to a method of using a medical clamp, the method including the steps of: providing a lower arm assembly and an upper arm assembly; connecting pivotally the upper arm assembly to the lower arm assembly; connecting a belt to the lower arm assembly and the upper arm assembly; forming a loop, using the belt, between the lower arm assembly and the upper arm assembly; and clamping the lower arm assembly and the upper arm assembly relative to one another.

An advantage of the present invention is that, in one form, it is directed to a uterine clamp, which can be called the Staggs Uterine Compression Clamp, or simply the clamp. The uterine clamp of the present invention is advantageously a handheld manual reusable instrument that can mechanically apply compressive pressure to the myometrium of the uterus and ultimately decrease blood loss due to the uterine atony during postpartum hemorrhage.

Another advantage is that the primary function of the uterine clamp is to quickly and temporarily control hemorrhage from the atonic uterus in the immediate postpartum period by mechanically compressing the myometrium of the uterus. The use of the device advantageously does not preclude the use of other methods of controlling hemorrhage such as uterotonic drugs. The compression of the myometrium is advantageously accomplished by two methods. The first is a set of upper and lower jaws (i.e., the upper and lower arm assemblies, below) designed to securely hold the uterus and compress the lower uterine segment. A second method of compression is an elastic strap (which is referred to as a belt, below) that is longitudinally oriented to compress the fundus of the uterus. This advantageously gives a more global compression to the myometrium and can quickly slow bleeding and prevent further blood loss. A secondary function of the uterine clamp advantageously is to retract the uterus during a Caesarean section. Using a conventional technique, the surgical assistant grasps the uterus and retracts the uterus out of the pelvis to give the surgeon a better view of the transverse uterine incision that was performed to remove the fetus and placenta; this maneuver is ergonomically difficult for the assistant. But, the uterine clamp of the present invention advantageously allows this retraction (and holding) of the uterus to occur with greater efficiency and less effort.

Yet another advantage of the present invention is that it provides a new way to rapidly control blood loss during postpartum hemorrhage caused by uterine atony.

Yet another advantage of the present invention is that it provides a rapid and effective adjunct to the usual procedures to control hemorrhage. Using the clamp according to the present invention does not preclude the other standard and aggressive measures that are usually performed.

Yet another advantage of the present invention is that it provides another way to slow or to stop the bleeding and, thus, provides another tool to save the life of the parturient.

Yet another advantage of the present invention is that it can be manufactured using standard manufacturing methods.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
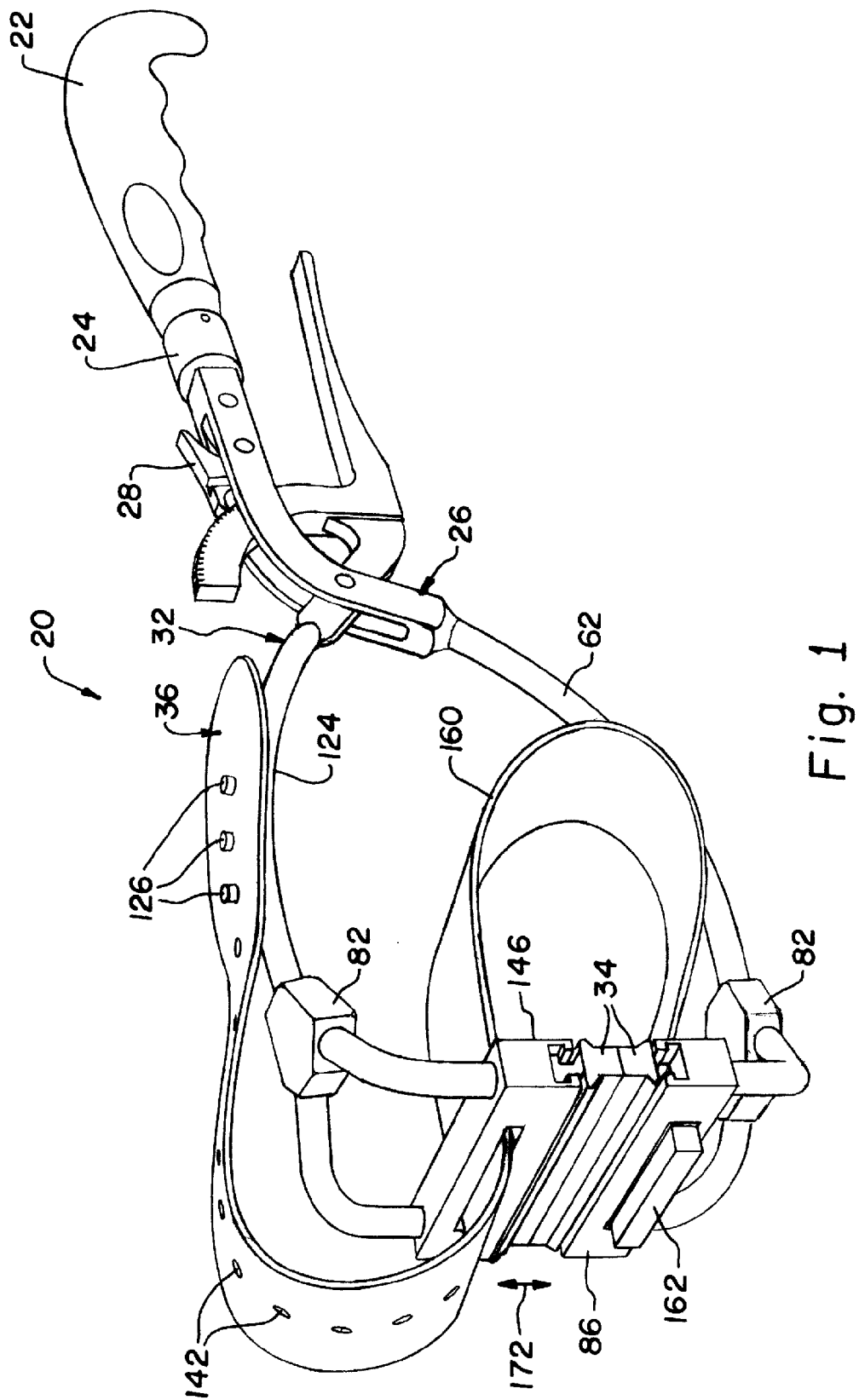
FIG. 1 is a perspective view of the uterine compression clamp according to the present invention.
Figure 2:
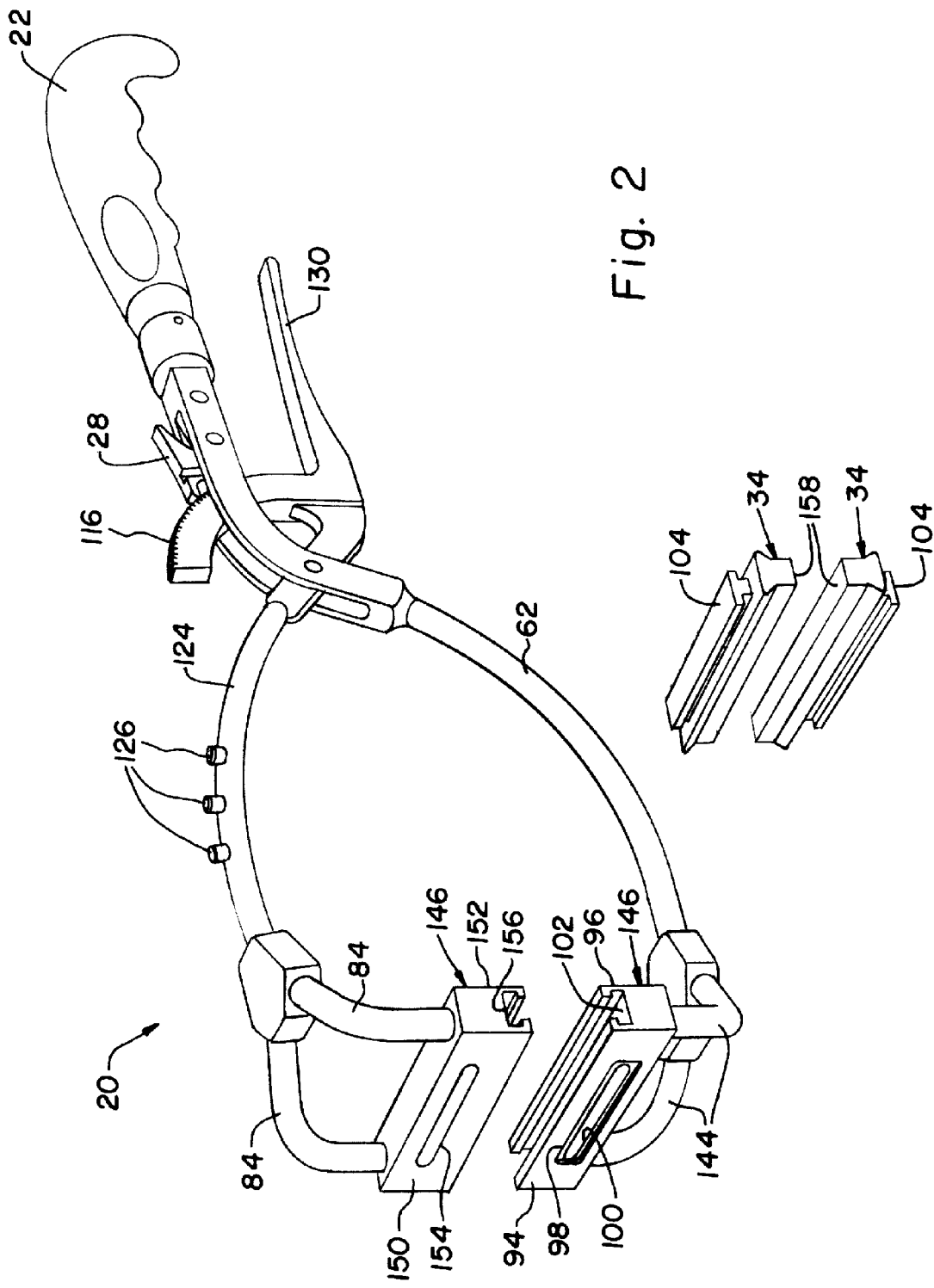
FIG. 2 is a perspective view of the uterine compression clamp of FIG. 1, with the grippers being exploded from the remainder of the clamp, but without the belt.

Referring now to the drawings, and more particularly to FIGS. 1-11, there is shown a first embodiment of a uterine compression clamp 20 according to the present invention. Clamp 20 (which can generally be referred to as a medical clamp) generally includes a handle 22, a post 24, a lower arm assembly 26, a release lever 28, a torsion spring 30, an upper arm assembly 32, two grippers 34, and a belt 36. In general, grippers 34 of clamp 20 can be selectively opened and closed, as indicated by double-arrow 172 in FIG. 1. Further, in general, belt 36 of clamp 20 can be tightened so as to compress at least a part of uterus 166, as indicated by arrow 176 in FIG. 4.

Handle 22 is used by a medical professional (such as an obstetrician/gynecologist, or, more generally, a surgeon, or other operating or delivery room personnel) to hold clamp 20. Handle 22 includes a body 38 and a distal end 40 including a cylindrical projection 42. Body 38 can include a geometry that is ergonomically efficient relative to the hand of a medical professional. Body 38 can include a core and a material molded over the core. By way of example and not by way of limitation, the core can be formed of a metal such as 304 stainless steel (DIN 1.4301) and have a finish as molded, and the material bonded over the core can be elastosil silicone. Distal end 40 can be a metal (as stated relative to the core) and can be formed integral with the core or can be connected to the core. The metallic core and distal end (whether formed integrally or separately) can be made using one or more machining operations, such as lathe machining and/or a milling machining operation (for example, blind hole 44 can be formed using a milling machine). Cylindrical projection 42 can include blind hole 44 extending transversely through projection 42; blind hole 44 can have a chamfered entry, have a generally cylindrical extension, and have a flat bottom. Projection 42 is received by post 24. Blind hole 44 has a cylindrical shape and can extend more than fifty percent through projection 42. Aside from hole 44, handle 22 can be substantially similar on the portion that is not visible in the figures as that portion which is visible in the drawings. By way of example and not by way of limitation, distal end 40 can be formed of a metal such as 304 stainless steel (DIN 1.4301) and have a finish that is polish satin. All metal components of handle 22 can be passivated prior to assembly per ASTM A-967.

Post 24 serves as a transition piece between handle 22 and lower arm assembly 26. Post 24 includes a proximal end (toward handle) and a distal end (toward grippers). The proximal end includes a receiver 46 having a blind hole formed therein, the blind hole (not shown in the drawings) of receiver 46 having a cylindrical shape and extending from a proximal face of receiver 46 (facing towards handle 22) longitudinally in a distal direction, the blind hole of receiver 46 being at least approximately centered in the proximal face of receiver 46. The blind hole of receiver 46 matingly receives projection 42 of handle 22; the blind hole of receiver 46 can be drilled (and be cone-shaped at the distal end of the blind hole that is not necessarily completely filled by projection 42 of handle 22). Receiver 46 also includes a through-hole 50 extending transversely from an exterior surface of receiver 46 to the blind hole in receiver 46. A cross pin 48 attaches receiver 46 of post 24 with projection 42 of handle 22; more specifically, after projection 42 is positioned in blind hole 50 of receiver 46, blind hole 44 of projection 42 and through-hole 50 (which holds cross pin 48) of receiver 46 are aligned, and cross pin 48 is inserted through this through-hole 50 of receiver 46 and into blind hole 44 of projection 42 so as to secure handle 22 and post 24 together. Aside from hole 50, post 24 can be substantially similar on the portion that is not visible in the figures as that portion which is visible in the drawings. By way of example and not by way of limitation, cross pin 48 can be 0.125 inches×0.275 inches and be formed of a metal such as 303 stainless steel. Through-hole 50 through receiver 46 can be formed by drilling. After inserting cross pin 48, cross pin 48 can be fuse welded in position, and cross pin 48 and/or the fuse weld can be polished flush with post 24 and passivated. By way of example and not by way of limitation, post 24 can be formed of a metal such as 17-4 PH stainless steel (condition H900) or DIN 1.4021 (heat treat and temper Rc 42-48), and post 24 can have a satin finish and be passivated. Post 24 can be made using one or more machining operations, such as lathe machining and/or a milling machining operation (for example, holes 48, 50, 54 can be formed using a milling machine). The distal end of post includes a projection 52 with a through-hole 54 extending transversely through projection 52 of post 24. Projection 52 of post 24 is secured to a proximal end of a base 60 of lower arm assembly 26 using a pin 56. More specifically, pin 56 is inserted through two proximal holes 58 of base 60 of lower arm assembly 26 and also through hole 54 of projection 52 of the distal end of post 24.

Figure 5:
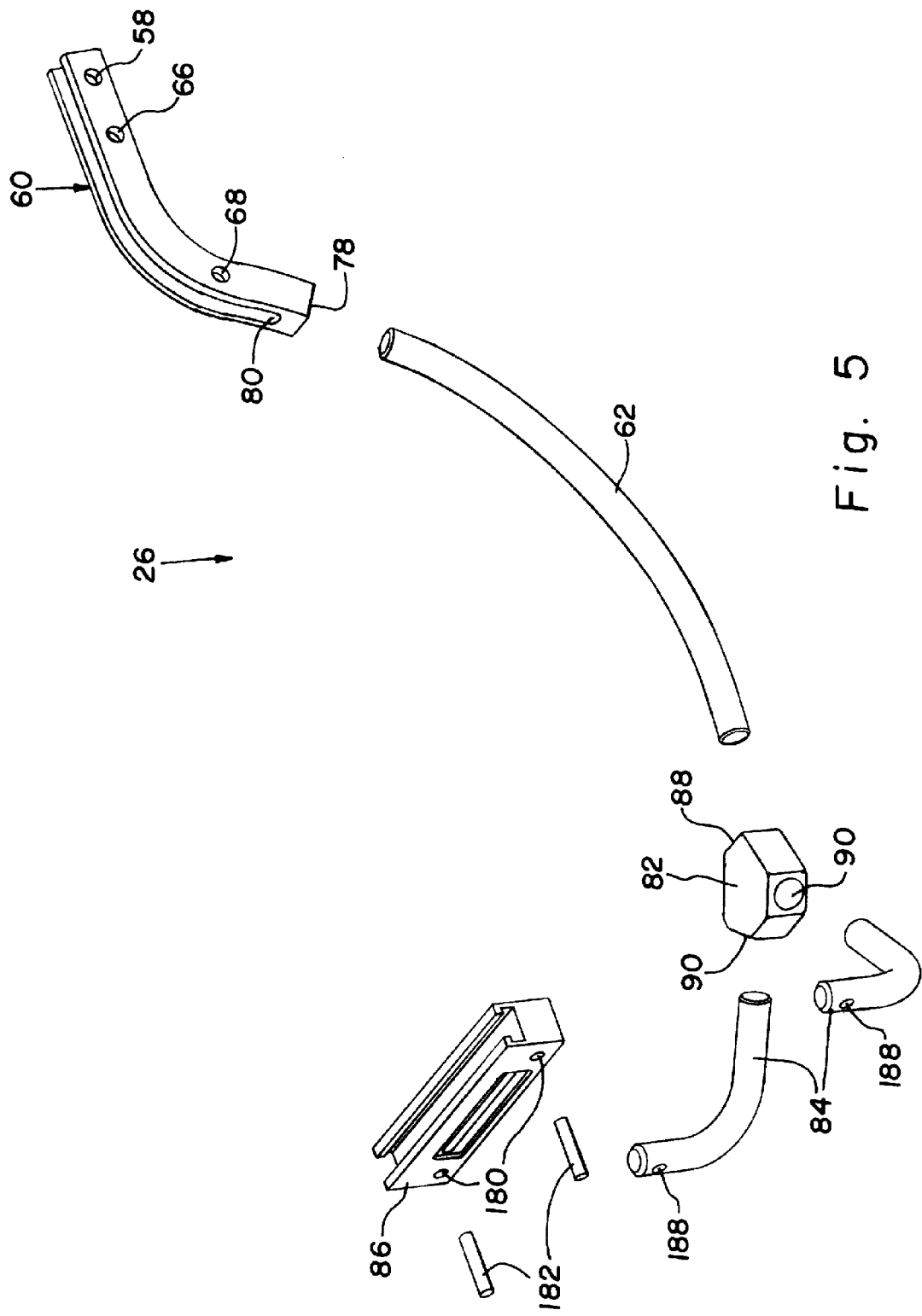
FIG. 5 is an exploded, perspective view of the lower arm assembly of the uterine compression clamp of FIG. 1, without the gripper.
Figure 6:
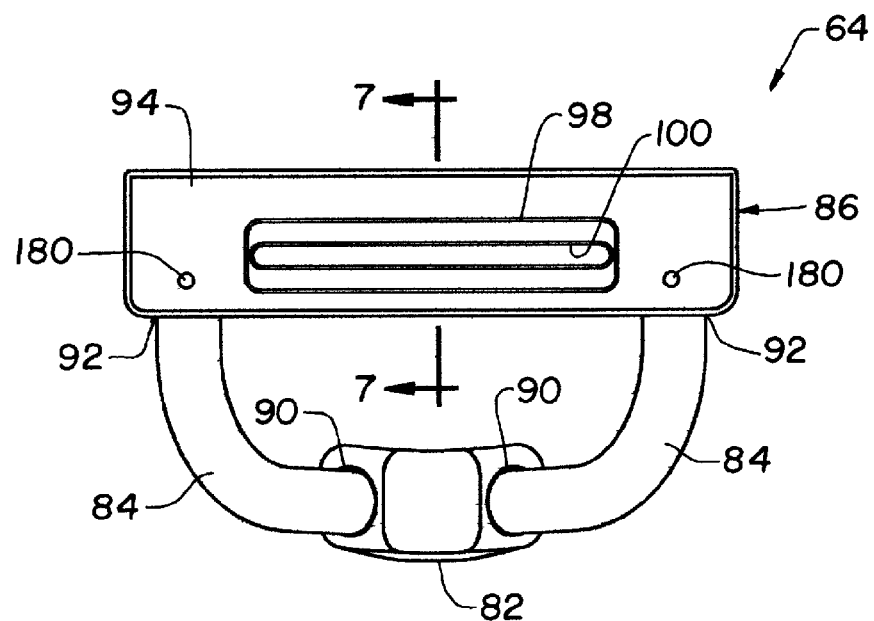
FIG. 6 is an end view of the lower tip sub-assembly of the uterine compression clamp of FIG. 1.
Figure 7:
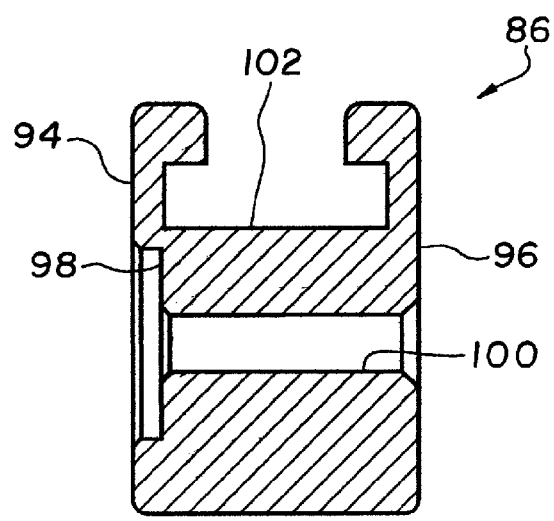
FIG. 7 is a cross-sectional view of the lower tip of the uterine compression clamp of FIG. 1, the cross-section being taken along line 7-7 of FIG. 6.
Figure 8:
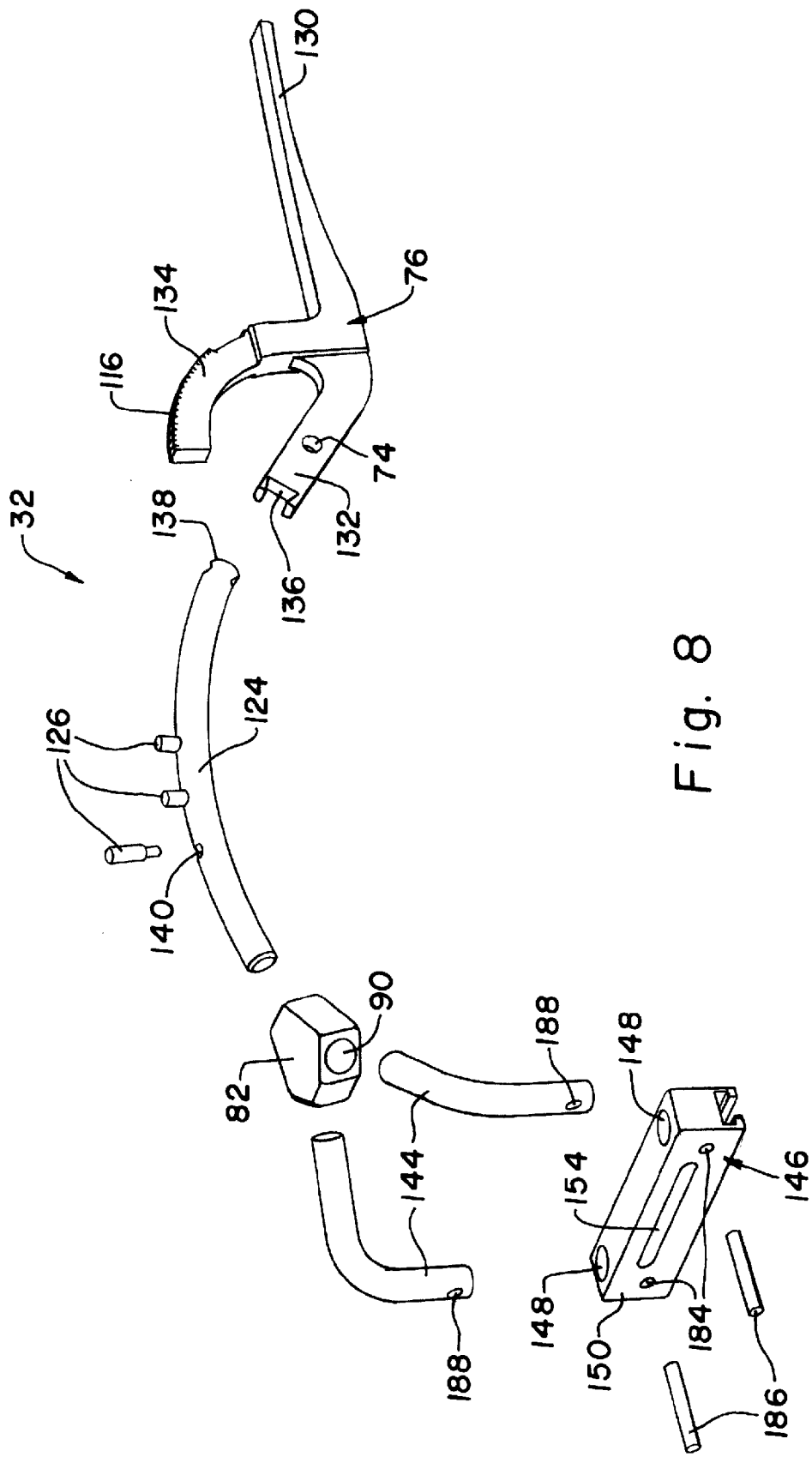
FIG. 8 is an exploded, perspective view of the upper arm assembly of the uterine compression clamp of FIG. 1, without the gripper.

Lower arm assembly 26 includes a base 60, a rod 62, and a tip sub-assembly 64. As shown in FIG. 5, base 60 includes two walls which run parallel to one another, each of these walls including two holes 58, 66 on the proximal end of base 60 and an additional hole 68 on the distal end of base 60. Holes 58 oppose one another. Holes 66 oppose one another. Holes 68 oppose one another. As discussed above, pin 56 extends through holes 58 of base 60 and hole 54 of post 24 to thereby attach post 24 to base 60 of lower arm assembly 26. Another pin 56 extends through holes 66 of base 60 and also through a hole 108 of release lever 28 to thereby attach release lever 28 (which can also be called a trigger) to base 60. Pins 56 in holes 58 and 66 can be substantially identical. By way of example and not by way of limitation, pins 56 can be 0.1875 inches×0.500 inches, and can be formed of a metal such as 18-8 stainless steel. Pins 56 can be laser welded to base 60 at each of the respective holes 58, 66, and the laser weldment and/or pins 56 can be polished flush with base 60. A pivot pin 72 extends through holes 68 of base 60 and also through a corresponding through-hole 74 of a base 76 of upper arm assembly 32 to thereby attach base 60 of lower arm assembly 26 to base 76 of upper arm assembly 32. By way of example and not by way of limitation, pivot pin 72 can be formed of a metal such as a wear resistant stainless steel, such as Nitronic 60, and can have a satin finish; the longitudinal ends of pivot pin 72 can be chamfered. Pivot pin 72 can be laser welded to base 60 of lower arm assembly at each of the respective holes 68, and the laser weldment and/or pivot pin 72 can be polished flush with lower base 60. The distal end of base 60 of lower arm assembly 26 includes material which has a blind hole 78 formed therein which opens at the distal face of base 60; blind hole 78 can have a chamfered entry, have a generally circular cross-section, and have a flat bottom. Blind hole 78 receives a proximal end of rod 62 of lower arm assembly 26 to thereby connect base 60 and lower rod 62 together. Base 60 can be substantially similar on the portion that is not visible in the figures as that portion which is visible in the drawings. At the connection of the proximal end of lower rod 62 and blind hole 78 of base 60, base 60 and lower rod 62 can be TIG (tungsten inert gas welding) welded together; an appropriate filler can be used at this connection. This weldment can be polish blended, and the weld areas can be passivated. Base 60 of lower arm assembly 26 has generally a U-shape formed by the parallel walls (which are the legs of the U, albeit curved legs) and a junction 80 in which blind-hole 78 is formed, the walls being attached to each other only by way of junction 80 at the distal end of base 60. By way of example and not by way of limitation, base 60 of lower arm assembly 26 can be formed of a metal such as 17-4 PH stainless steel (condition H900) or DIN 1.4021 (heat treat and temper Rc 42-48), and the finish can be a satin finish. Lower base 60 can be passivated. Lower base 60 can be formed by using a casting operation, by using a metal injection molding procedure, and/or by using one or more machining operations such as a milling machining operation and/or one or two wire Electrical Discharge Machining (EDM) operations. Lower rod 62 is a longitudinally extending lower rod but yet generally has a U-shape. Rod 62 of lower arm assembly 26 can be solid throughout and generally have a circular cross-section. Lower rod 62 can be substantially similar on the portion that is not visible in the figures as that portion which is visible in the drawings. By way of example and not by way of limitation, lower rod 62 can be formed of a metal such as 17-4 PH stainless steel (condition H900) or DIN 1.4021 (heat treat and temper Rc 42-48), and the finish can be a satin finish. Lower rod 62 can be passivated. Lower rod 62 can be formed using a lathe machining operation and then shaped by bending.

Tip sub-assembly 64 of lower arm assembly 26 includes a coupler 82, two curved lateral arms 84, and a tip 86. Coupler 82 (which can also be referred to as a union) includes three blind holes 88 and 90, and can otherwise be solid throughout. One hole 88 of coupler 82 matingly receives and is thereby attached to the distal end of lower rod 62. Hole 88 can have a chamfered entry, have a generally cylindrical extension, and have a cone-shaped bottom, the point of the cone extending away from the opening of hole 88. Two holes 90 of coupler 82 matingly receive and are thereby attached respectively to the proximal ends of lateral arms 84. Each hole 90 can respectively have a flat bottom away from the openings of holes 90. Each hole 90 can have a chamfered entry, have a generally cylindrical extension, and have a flat bottom. Holes 88, 90 of coupler 82 can be generally directed towards each other and thus towards a center of coupler 82. Coupler 82 can be slightly arc-shaped about a longitudinal axis centered and running through hole 88, the arc shape being open facing upwardly generally towards upper arm assembly 32. By way of example and not by way of limitation, coupler 82 can be formed of a metal such as 17-4 PH stainless steel (condition H900) or DIN 1.4021 (heat treat and temper Rc 42-48), and the finish can be a satin finish. Coupler 82 can be passivated. Coupler 82 can be made using a machining operation such as a milling machining operation. Coupler 82 can be TIG welded to distal end of lower rod 62 by way of hole 88. Each lateral arm 84 can be solid throughout. Coupler 82 can be TIG welded to proximal ends of lateral arms 84 respectively by way of the two holes 90. The distal ends of each lateral arm 84 attaches to a lateral portion of lower tip 86 to thereby provide lateral support to lower tip 86. More specifically, the lateral side portions of the bottom surface of lower tip 86 include two blind holes 92 which matingly receive the distal ends of each lateral arm 84 of tip sub-assembly 64. Lateral arms 84 provide lateral strength to lower tip 86. The distal ends of each lateral arm 84 can each include a through-hole 188, the position of through-holes 188 being approximately shown in FIG. 5. Lateral arms 84 can be solid throughout. Lateral arms 84 are substantially similar to one another. By way of example and not by way of limitation, each lateral arm 84 can be formed of a metal such as 17-4 PH stainless steel (condition H900) or DIN 1.4021 (heat treat and temper Rc 42-48), and the finish can be a satin finish. Each lateral arm 84 can be passivated. Lateral arms 84 can be formed using a lathe machining operation and then shaped by bending, holes 188 optionally being formed by a milling machining operation. Each blind hole 92 of lower tip 86 can have a chamfered entry, have a generally cylindrical extension, and have a flat bottom. Lower tip 86 is coupled with, and extends transversely relative to, lower rod 62. More specifically, lower tip 86 includes a distal face 94 and a proximal face 96, each of which extends generally transversely to a longitudinal axis of clamp 20 (the longitudinal axis extending through handle 22 and post 24 and distally therefrom). Distal face 94 includes a transversely extending channel 98. Lower tip 86 includes a slot 100 (which can be called a lower slot) which forms a through-hole through lower tip 86 running from channel 98 to proximal face 96 of lower tip 86. Stated another way, lower slot 100 extends from proximal face 96 of lower tip 86 to channel 98 of distal face 94 of lower tip 86. Belt 36 extends all of the way through lower tip 86 from the distal side of lower tip 86 to the proximal side of lower tip 86 by way of channel 98 and slot 100. Slot 100 can flare outwardly (i.e., chamfered) starting near proximal face 96 and terminating at proximal face 96 to thereby increase the cross-sectional area of slot 100 near proximal face 96. Channel 98 can be used to at least partially receive stop 162 of belt 36. Lower tip 86 also includes a female dovetail 102 (which can also be referred to as a receiving slot or as a T-slot) for matingly receiving a male dovetail (which can also be referred to as a T-section) of a respective gripper 34. Female dovetail 102 (the T-slot 102) can be formed, at least in part, by breaking the edges of T-slot 102 at both ends of lower tip 86 so that T-slot 102 does not have any sharp edges, as sharp edges could tear into or otherwise damage a respective gripper 34 received by T-slot 102. Female dovetail 102 extends the transverse width of lower tip 86; in this way, a respective gripper 34 can be slid into female dovetail 102 from either lateral side of lower tip 86. Lower tip 86 includes through-holes 180 which pass through blind holes 92 from distal face 94 to proximal face 96; holes 180 can be formed by a milling machining operation. Other than channel 98 formed in distal face 94 of lower tip 86, the proximal and distal faces 94, 96 of lower tip 86 are substantially identical. Further, the transverse sides of lower tip 86 are substantially identical. By way of example and not by way of limitation, lower tip 86 can be formed of a metal such as 17-4 PH stainless steel (condition H900) or DIN 1.4021 (heat treat and temper Rc 42-48), and the finish can be a satin finish. Lower tip 86 can have a 63 Ra surface finish. Lower tip 86 can be passivated. Lower tip 86 can be formed using a milling machining operation (to include channel 98) and slot 100 and T-slot 102 can be formed using a wire EDM operation. Each weldment (lower rod 62 to coupler 82; coupler 82 to each lateral arm 84) can use an appropriate filler, can be polished, and each such weld area can be passivated. Two cross-pins 182 can be used to secure a respective lateral arm 84 to a respective blind hole 92 of lower tip 86; for example, a cross-pin 182 is inserted from either distal face 94 or proximal face 96 to the opposing distal face 94 or proximal face 96 using hole 180 in lower tip 86 and hole 188 of lateral arm 84 after the distal end of lateral arm 84 is positioned in blind hole 92 and holes 180 and 188 are aligned. After pinning holes 180 and 188 of lower tip 86, cross pins 182 can be laser welded to holes 180 and/or holes 188, and both sides of lower tip 86 can be polished flush relative to this laser weldment. By way of example and not by way of limitation, cross pins 182 can be formed of a metal such as DIN 1.4021 or 420 stainless steel. Lower arm assembly 26 further includes a lower gripper 34 attached to lower tip 86; lower gripper 34 is discussed further below.

Release lever 28 includes a loop 106 which defines a through-hole 108. Release lever 28 is secured to base 60 of lower arm assembly 26 by way of a pin 56 through hole 108 of loop 106 and opposing holes 58 of base 60 of lower arm assembly 26. Release lever 28 further includes a pressing section 110, a stop portion 112, and a channel 114. Pressing section 110 is configured for being pressed down by the surgeon (i.e., by the thumb of the surgeon) to release stop portion 112 from the grooves between the teeth 116 of upper arm assembly 32. Stop portion 112 is configured for being lodged between teeth 116 so as to lock upper arm assembly 32 in place relative to lower arm assembly 26. Stated another way, release lever 28 is used to selectively engage or release stop portion 112 relative to teeth 116 so that grippers 34 can be moved toward or away from each other to selectively clamp the uterus 166 therebetween or to release the hold on uterus 166 from therebetween. Channel 114 is formed between pressing section 110 and stop portion 112 of release lever 28. Channel 114 receives an arm 118 of torsion spring 30. By way of example and not by way of limitation, release lever 28 can be formed of a metal such as 17-4 PH stainless steel (condition H900) or DIN 1.4021 (heat treat and temper Rc 42-48), and the finish can be a satin finish. Release lever 28 can have a 63 Ra surface finish. Release lever 28 can be passivated completely.

Figure 3:
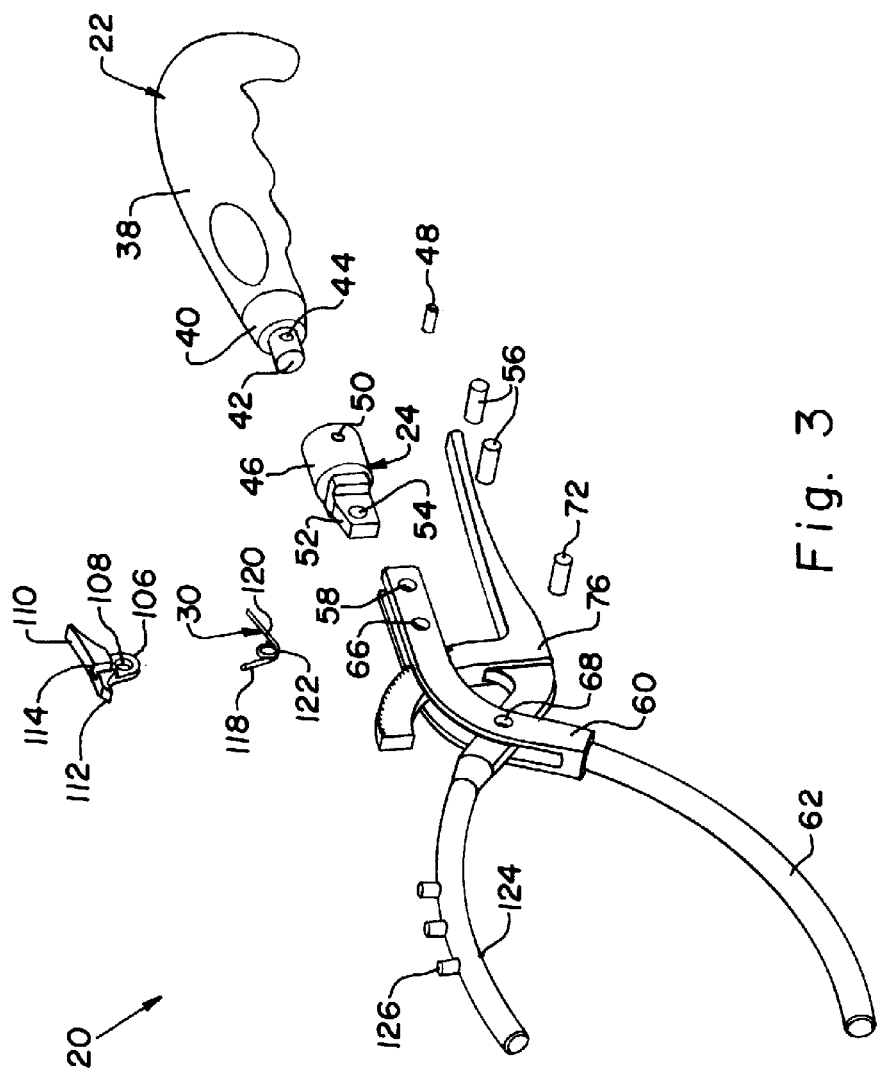
FIG. 3 is an exploded, perspective view of the uterine compression clamp of FIG. 1, without the grippers or the belt.
Figure 3:
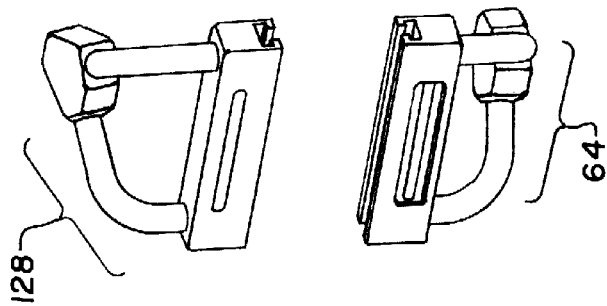

Torsion spring 30 includes a loop 122 and two arms 118, 120, one arm 118 projecting generally upwardly, the other arm 120 projecting back towards handle 22 (more specifically, back to post 24). Pin 56 extends through not only through-holes 66 in base 60 of lower arm assembly 26 but also through loop 122 of torsion spring 30 and loop 106 of release lever 28 to secure both release lever 28 and torsion spring 30 to base 60. The arm 118 projecting generally upwardly lies in channel 114. The arm 120 projecting back towards post 24 lies against post, such as against a distal face of projection 52 of post 24 or against the top face (which is shown in FIG. 3 as being slanted upwardly running in a proximal direction of the top face) of projection 52 of post 24; this top face (which is slanted) of post 24 can have an angle of 15°, 20°, 25°, or 30°, or whatever degree of slant is deemed suitable. Torsion spring 30 biases release lever 28 into a locked position against the grooves between teeth 116. The surgeon's pressure (such as thumb pressure) on pressing section 110 of release lever 28 can overcome this biasing pressure of torsion spring 30 to release release lever 28 from teeth 116. Once release lever 28 is released from teeth 116, the surgeon can selectively open or close clamp 20. Similarly, squeezing proximal projection 130 of upper arm assembly 32 may be able to cause stop portion 112 of release lever 28 to move downwardly (in a clockwise direction when viewing FIG. 4) along upper projection 134 of upper arm assembly 32. When pressing section 110 of release lever 28 is pressed down to release stop portion 112 from teeth 116, the placement of stop portion 112 on upper projection 134 of upper arm assembly 32 can be adjusted, such as by moving stop portion 112 in a counter-clockwise direction (viewed in FIG. 4) along upper projection 134 of upper arm assembly 32 by moving proximal projection 130 of upper arm assembly 32 away from handle 22 (stop portion 112 can also be moved in a clockwise direction (viewed in FIG. 4) along upper projection 134 when pressing section 110 is pressed downwardly so as to release stop portion 112 from teeth 116). This adjustment using release lever 28 causes grippers 34 to selectively spread apart or move closer together relative to one another and thereby to clamp or release tissue (i.e., that of the uterus 166); stated another way, clamp 20 can be selectively opened and closed in this manner. Teeth 116 enable grippers 34 to be locked into place in predetermined positions relative to one another. Torsion spring 30 can be a McMaster Carr product, such as product 9287K28 and be a type 302 stainless steel.

The upper arm assembly 32 includes an upper base 76, a rod 124, a plurality of pins 126, and a tip sub-assembly 128. Upper arm assembly 32 is pivotally connected to lower arm assembly 26, lower arm assembly 26 and upper arm assembly 32 being configured for clamping relative to one another. The upper base 76 includes a proximal projection 130 serving as a piece which can be gripped by the surgeon along with handle 22 and selectively moved towards handle 22 as proximal projection 130 is squeezed by the surgeon or moved away from handle 22; double-arrow 174 shows the directions in which proximal projection 130 can be moved. Upper base 76 also includes a distal end projection 132 which connects to upper rod 124 of upper arm assembly 32, distal end projection 132 including a female dovetail 136 for receiving a male dovetail projection 138 of the proximal end of upper rod 124 of upper arm assembly 32 (male dovetail projection 138 can be slidingly received by female dovetail 136 during assembly of clamp 20). Distal end projection 132 further includes through-hole 74 for receiving pivot pin 72, pivot pin 72 thereby connecting lower and upper arm assemblies 26, 32 together and allowing lower and upper arm assemblies 26, 32 to pivot relative to each other to selectively clamp and release an object, such as a uterus 166. Upper base 76 further includes an upper projection 134 which is generally arched and includes a plurality of teeth 116, teeth 116 being configured for serving as stops to hold release lever 28 in place selectively at predetermined positions. Teeth 116 can be formed by a wire EDM operation, the finish of the teeth can be such that a glass bead blasting can be used to remove an EDM scale within the teeth. Upper base 76 can be substantially similar on the portion that is not visible in the figures as that portion which is visible in the drawings. By way of example and not by way of limitation, base 76 of upper arm assembly 32 can be formed of a metal such as 17-4 PH stainless steel (condition H900) or DIN 1.4021 (heat treat and temper Rc 42-48), and the finish can be a satin finish. Upper base 76 can be passivated. Upper base 76 can be formed by using a casting operation, by using a metal injection molding procedure, and/or by using one or more machining operations such as a milling machining operation and/or one or two wire EDM operations. At the connection of the proximal end of upper rod 124 and distal end projection 132 of upper base 76, upper base 76 and upper rod 124 can be TIG welded together where the male and female dovetails 136, 138 (of upper rod 124 and distal end projection 132 of upper base 76, respectively) connect to one another; an appropriate filler can be used at this connection. This weldment can be polish blended, and the weld areas can be passivated. Upper rod 124 is a longitudinally extending lower rod but yet generally has a U-shape. Rod 124 of upper arm assembly 32 can be solid throughout and generally have a circular cross-section. The proximal end of upper rod 124 includes male dovetail projection 138, which is received during assembly by female dovetail projection 136 of distal end projection 132 of upper base 76. By way of example and not by way of limitation, upper rod 124 can be formed of a metal such as 17-4 PH stainless steel (condition H900) or DIN 1.4021 (heat treat and temper Rc 42-48), and the finish can be a satin finish. Upper rod 124 can be passivated. Upper rod 124 can be formed using a lathe machining operation and then shaped by bending; pin holes 140 can be formed in upper rod 124 using a milling machining operation; and male dovetail 138 of upper rod 124 can optionally be formed by a wire EDM operation. Upper rod 124 includes three pin holes 140 spaced apart along upper rod 124; upper rod 124 can have more or less pin holes 140. Pin holes 140 can be through-holes extending from a top-dead centerline of upper rod 124 to a bottom-dead centerline of upper rod 124. Pin holes 140 can have a stepped configuration. Each pin hole 140 can have a circular cross-section, and the stepped configuration of each pin hole 140 can have a greater diameter in substantially the top half of pin hole 140 and a lesser diameter in substantially the bottom half of pin hole 140 (the top half being that portion of upper rod 124 to which belt 36 is attached by way of pins 126); the step of each pin hole 140 can be positioned at about midway along the diameter of upper rod 124. Viewed from the side and where each of pin holes 140 are positioned, upper rod 124 can have a slight divot on the top surface and an even smaller divot on the bottom surface. Upper rod 124 includes a plurality of pins 126 projecting generally upwardly from upper rod 124. Pins 126 can thus have a mating stepped configuration relative to pin holes 140, each of pins 126 having a top portion diameter which is greater than a bottom portion diameter, the top portion with the greater diameter having a greater length than the bottom portion having a smaller diameter. Besides the stepped diameter of pin 126, each pin 126 has a generally cylindrical shape (as do through-holes 140 matingly receiving pins 126). Pins 126 extend above the top surface of upper rod 124 so that belt holes 142 can be secured over pins 126 and thereby belt 36 can be held to upper rod 124. By way of example and not by way of limitation, pins 126 can be formed of a metal such as 17-4 PH stainless steel (condition H900) or DIN 1.4021 (heat treat and temper Rc 42-48), and the finish can be a satin finish. Pins 126 can have a 63 Ra surface finish. Pins 126 can be passivated. Pins 126 can be bonded to holes 140 and/or can form an interference fit or press fit with holes 140. Pins 126 can be laser welded to the top surface of upper rod 124 where pins 126 project above the top surface of upper rod 124 to receive belt holes 142. These weldments can be polished and passivated. Further, pins 126 can be TIG welded to the bottom surface of upper rod 124 all around the bottom of holes 140, and these weldments can be polished and passivated; more specifically, these weldments to the bottom surface of upper rod 124 can be polished flush with the bottom surfaced of upper rod 124. Thus, pins 126 serve to hold belt 36 using belt holes 142, as described below. Upper rod 124 can be substantially similar on the portion that is not visible in the figures as that portion which is visible in the drawings.

Tip sub-assembly of upper arm assembly includes another coupler 82, two curved lateral arms 144, and a tip 146. Coupler 82 of tip sub-assembly 128 of upper arm assembly 32 is substantially identical to coupler 82 of tip sub-assembly 64 of lower arm assembly 26, but the arc of the upper coupler 82 is open downwardly generally towards lower arm assembly 26. Hole 88 of coupler 82 of upper arm assembly 32 matingly receives and is thereby attached to the distal end of upper rod 124. Holes 90 matingly receive and are thereby attached respectively to the proximal ends of lateral arms 144. Coupler 82 of upper arm assembly 32 can be TIG welded to the distal end of upper rod 124 by way of hole 88. Each lateral arm can be solid throughout. Coupler 82 of upper arm assembly 32 can be TIG welded to the proximal ends of lateral arms 144 respectively by way of the two holes 90. The distal ends of each lateral arm 144 attaches to a lateral portion of upper tip 146 to thereby provide lateral support to upper tip. More specifically, the lateral side portions of the upper surface of upper tip 146 include two blind holes 148 which matingly receive the distal ends of each lateral arm 144. Lateral arms 144 provide lateral strength to upper tip 146. The distal ends of each lateral arm 144 can each include a through-hole 188, the position of through-holes 188 being approximately shown in FIG. 8. Lateral arms 144 can be solid throughout. Lateral arms 144 are substantially similar to one another. By way of example and not by way of limitation, each lateral arm 144 can be formed of a metal such as 17-4 PH stainless steel (condition H900) or DIN 1.4021 (heat treat and temper Rc 42-48), and the finish can be a satin finish. Each lateral arm 144 can be passivated. Lateral arms 144 can be formed using a lathe machining operation and then shaped by bending, holes 188 optionally being formed by a milling machining operation. Each blind hole 148 of upper tip 146 can have a chamfered entry, have a generally cylindrical extension, and have a flat bottom. Upper tip 146 is coupled with, and extends transversely relative to, upper rod 124. More specifically, upper tip 146 includes a distal face 150 and a proximal face 152, each of which extends generally transversely to the longitudinal axis of clamp 20. Upper tip 146 includes a slot 154 (which can be called an upper slot) which forms a through-hole through upper tip 146 running from distal face 150 to proximal face 152 of upper tip 146. Stated another way, upper slot 154 extends from proximal face 152 of upper tip 146 to distal face 150 of upper tip 146. Slot 154 can flare outwardly (i.e., chamfered) starting near proximal face 152 and terminating at proximal face 152 to thereby increase the cross-sectional area of slot near proximal face; slot 154 can similarly flare (i.e., chamfered) relative to distal face 150. Belt 36 extends all of the way through upper tip 146 from proximal face 152 of upper tip 146 to distal face 150 of upper tip 146 by way of slot 154. Upper tip 146 also includes a female dovetail 156 (which can also be referred to as a receiving slot or as a T-slot) for matingly receiving a male dovetail 104 of a respective gripper 34. Female dovetail 156 extends the transverse width of upper tip 146; in this way, a respective gripper 34 can be slid into female dovetail 156 from either lateral side of upper tip 146. Female dovetail 156 (the T-slot 156) can be formed, at least in part, by breaking the edges of T-slot 156 at both ends of upper tip 146 so that T-slot 156 does not have any sharp edges, as sharp edges could tear into or otherwise damage a respective gripper 34 received by T-slot 156. Upper tip 146 includes through-holes 184 which pass through blind holes 148 from distal face 150 to proximal face 152; holes 184 can be formed by a milling machining operation. The proximal and distal faces 150, 152 of upper tip 146 are substantially identical. Further, the transverse sides of upper tip 146 are substantially identical. By way of example and not by way of limitation, upper tip 146 can be formed of a metal such as 17-4 PH stainless steel (condition H900) or DIN 1.4021 (heat treat and temper Rc 42-48), and the finish can be a satin finish. Upper tip 146 can have a 63 Ra surface finish. Upper tip 146 can be passivated. Upper tip 146 can be formed using a milling machining operation and slot 154 and T-slot 156 can be formed using a wire EDM operation. Each weldment (upper rod 124 to coupler 82 of upper arm assembly 32; coupler 82 of upper arm assembly 32 to each lateral arm 144) can use an appropriate filler, can be polished, and each such weld area can be passivated. Two cross-pins 186 can be used to secure a respective lateral arm 144 to a respective blind hole 148 of upper tip 146; for example, a cross-pin 186 is inserted from either distal face 150 or proximal face 152 to the opposing distal face 150 or proximal face 152 using hole 184 in upper tip 146 and hole 188 of lateral arm 144 after the distal end of lateral arm 144 is positioned in blind hole 148 and holes 184 and 188 are aligned. After pinning holes 184 and 188 of upper tip 146, cross pins 186 can be laser welded to holes 184 and/or holes 188, and both sides of upper tip 146 can be polished flush relative to this laser weldment. By way of example and not by way of limitation, cross pins 186 can be formed of a metal such as DIN 1.4021 or 420 stainless steel. Upper arm assembly 32 further includes an upper gripper 34 attached to upper tip 146; upper gripper 34 is discussed further below.

Figure 4:
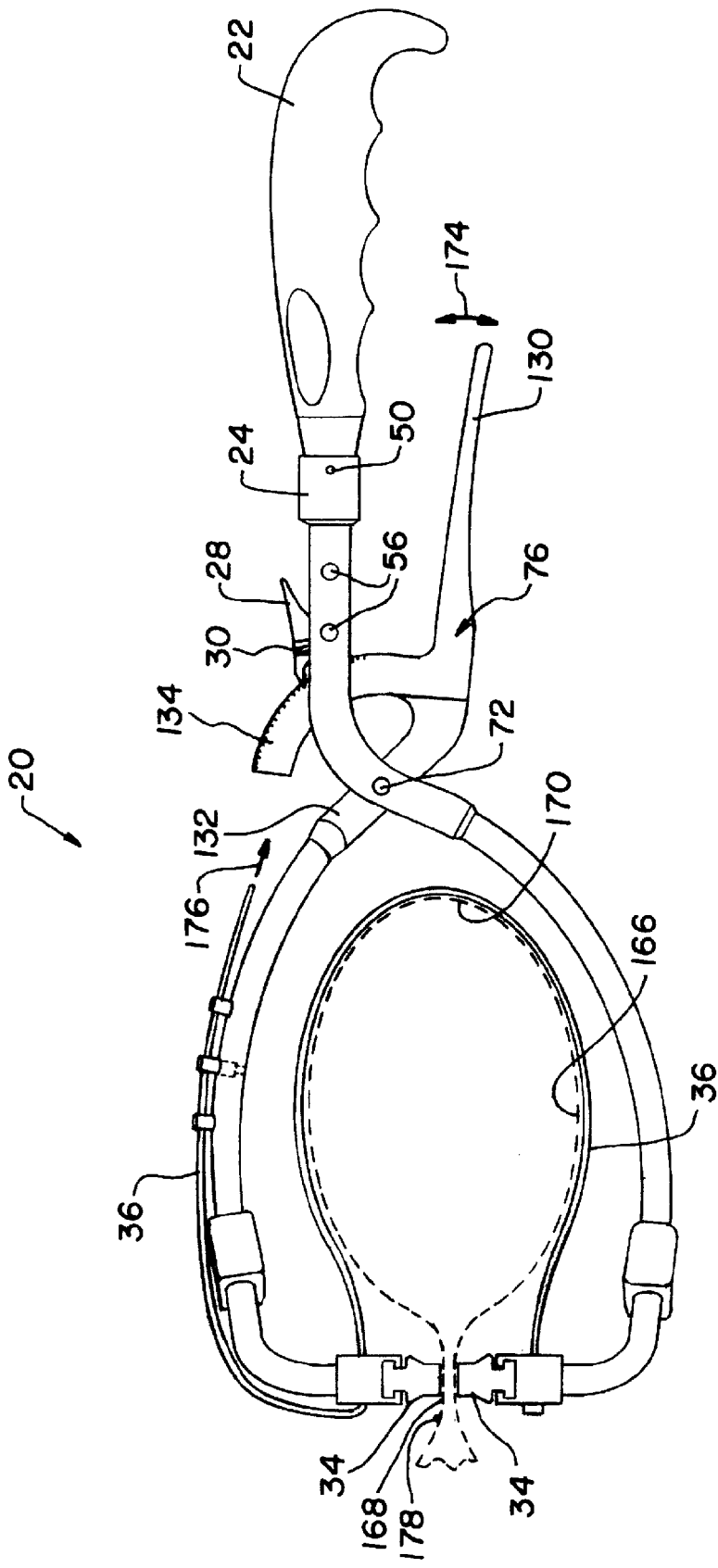
FIG. 4 is a side view of the uterine compression clamp of FIG. 1.
Figure 9:
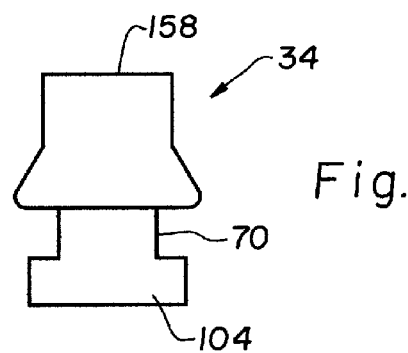
FIG. 9 is a side view of a gripper of the uterine compression clamp of FIG. 1.
Figure 10:
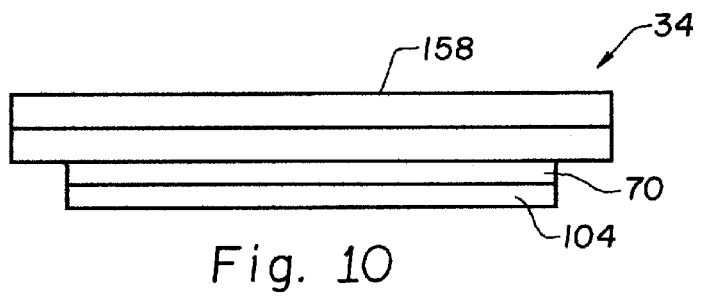
FIG. 10 is an end view of a gripper of the uterine compression clamp of FIG. 1.

Grippers 34 are used to contact and clamp therebetween a lower uterine segment 168. FIGS. 9 and 10 show one gripper 34, each gripper 34 being at least substantially similar to one another. Thus, lower gripper 34 and upper gripper 34 (lower gripper 34 being associated with lower arm assembly 26 and upper gripper 34 being associated with upper arm assembly 32) are substantially identical to one another. Upper and lower grippers 34 are configured for clamping therebetween a lower uterine segment 168. It is understood that FIG. 10 shows either the proximal or the distal end view of gripper 34, both end views being substantially similar to one another. Further, it is understood that FIG. 9 shows either lateral side view of gripper 34, both lateral side views of gripper 34 being substantially similar to one another. Gripper 34 includes a male dovetail 104 which mates with a corresponding female dovetail slot 102, 156 of either tip 86, 146 of lower and upper arm assemblies 26, 32. Male dovetail 104 of grippers 34 can be slid into female dovetails 102, 156 of lower and upper tips 86, 146 and prevented from sliding out of female dovetails 102, 156 by way of a friction fit (i.e., by way of a stickiness of grippers 34 provided by the silicone); it is understood that grippers 34 can be removed from tips 86, 146 and replaced with a new set of grippers 34. Gripper 34 also includes a contact portion 158. Contact portion 158 serves to clamp a portion of the uterus 166 between respective contact portions 158 of opposing grippers 34. FIG. 4 shows opposing grippers 34 with their respective contact portions 158 clamping a portion (such as a lower uterine segment 168) of uterus 166 therebetween (grippers 34 and uterus 166 are not necessarily shown proportionally to size). Grippers 34 of clamp 20 can meet and be at least substantially parallel when grippers 34 are assembled on clamp 20 and clamp 20 is closed. By way of example and not by way of limitation, each gripper 34 can be formed of a material such as a silicone rubber, such as Wacker 407/70 (i.e., Elastosil R 407/70) or Wacker 407/70A and have a gloss finish (U.S. provisional application 61/361,994 listed material for the gripper therein as 917TK, which is a supplier number for a blended material having silicone rubber as base material). Additives such as a color pigment and/or a radiopaque substance can be provided to gripper 34 material so that gripper 34 has a certain color (i.e., black) and so that gripper 34 is viewable by way of, for example, an X-ray machine. For example (and not by way of limitation), a supplier's material (i.e., A70018BLK1 of supplier Medical Elastomer Development) containing 1% black pigment and 5% barium sulfate can be added to the aforementioned Wacker material, or the gripper 34 material itself can include these components in such overall proportions. Gripper 34 can be secured to a respective T-slot 102, 156 using a friction fit between gripper 34 and the respective T-slot 102, 156 (a press fit between gripper 34 and the respective T-slot 102, 156 is not necessarily used). Gripper includes a slot 70 which receives a portion of lower and upper tips 86, 146 to hold gripper 34. Gripper 34 can be made by heating up the material of gripper 34 and shooting the heated material through an extrusion tool and thereby extruding the gripper 34 (each piece can be extruded to size, or, if necessary, the process can include cutting the material to size after extrusion). Alternatively, gripper 34 can be made by injection molding. When clamp 20 is closed, grippers 34 can provide a substantially even amount of pressure across the length of grippers 34, or can, alternatively, provide more pressure in the regions of the lateral sides. When clamp 20 is closed, grippers 34 meet and are parallel relative to one another.

Figure 11:
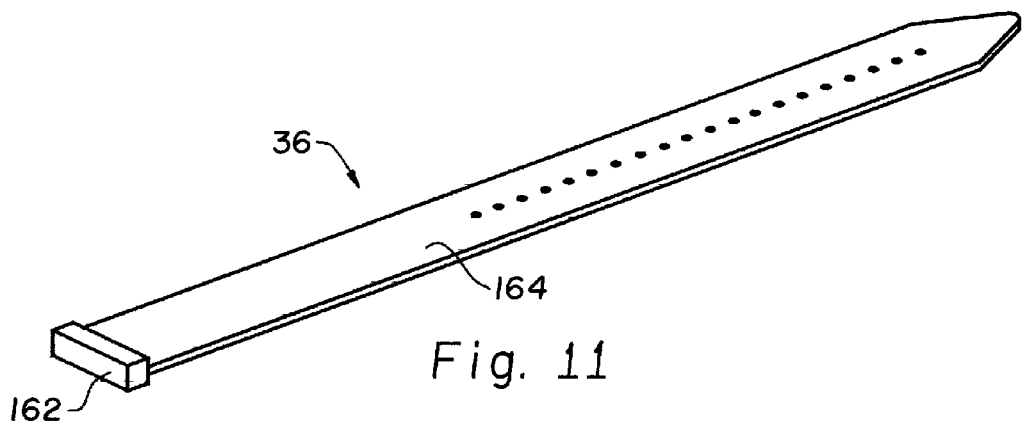
FIG. 11 is a perspective view of the belt of the uterine compression clamp of FIG. 1.

Belt 36 is connected to lower arm assembly 26 and upper arm assembly 32 and is configured for forming a loop 160 between lower arm assembly 26 and upper arm assembly 32. FIGS. 1, 4, and 11 show belt 36 of uterine clamp assembly 20 of the present invention. Belt 36 includes a body 164 with a plurality of through-holes 142. Through-holes 142 are spaced apart relative to one another. FIG. 11 shows that belt 36 can include twenty through-holes 142, but it is understood that belt 36 can include more or less such through-holes. Holes 142 are positioned over pins 126 and thereby lock belt 36 in predetermined positions. The plurality of holes 142 are thus configured for being selectively attached to the plurality of pins 126 and thereby for adjusting a size of loop 160, loop 160 being configured for compressing a portion of a uterus 166, that portion being generally a fundus 170 of uterus 166. Belt 36 also includes a stop 162. Stop 162 is positioned on one end of belt 36. Stop 162 is positioned adjacent channel 98 (and can be at least partially received by channel 98) and serves to prevent the end of belt 36 which has stop 162 from passing through lower slot 100 of lower tip 86 of lower arm assembly 26. Body 164 of belt 36 extends through lower slot 100 and through upper slot 154. Belt 36 can be elastic and can be made of, for example, rubber. Further, by way of example and not by way of limitation, belt 36 can be formed of a material such as silicone rubber, such as Momentive Tufel 94605 (which is understood to be a low volatile extrusion heat cured rubber), and have a matte finish (U.S. provisional application 61/361, 994 listed material for the belt therein as 917TL, which is a supplier number for a blended material having silicone rubber as base material). Additives such as a color pigment and/or a radiopaque substance can be provided to belt 36 material so that belt 36 has a certain color (i.e., black) and so that belt 36 is viewable by way of, for example, an X-ray machine. For example (and not by way of limitation), a supplier's material (i.e., A60017BLK1 of supplier Medical Elastomer Development) containing 1% black pigment and 5% barium sulfate can be added to the aforementioned Momentive material, or the belt 36 material itself can include these components in such overall proportions. Belt 36 can be made using a transfer molding process. By way of example and not be way of limitation, belt 36 can be approximately 1.56 inches in width, 20 inches in length, and 0.062 inches in thickness (the thickness referencing body 164, not stop 162), and stop 162 can have an approximately square cross-section).

FIG. 4 shows belt 36 in a solid line and shows uterus 166 schematically in broken lines. Belt 36 is shown with stop 162 being stopped by lower tip 86, belt 36 proceeding through slot 100 of lower tip 86 (in a distal to a proximal direction), then into the space between lower and upper rods 62 and 124 and encircling uterus 166 (in broken lines), belt 36 then proceeding through slot 154 of upper tip 146 (in a proximal to a distal direction), then to the outside of upper tip sub-assembly 128 and upper rod 124 and proceeding along upper rod 124 in a distal to a proximal direction, belt 36 then being selectively seated over pins 126 in three of belt holes 142. The tightness of belt 36 over uterus 166 can be selectively tightened or loosened by the surgeon by adjusting which belt holes 142 pins 126 are inserted therethrough. Uterus 166 is shown schematically being clamped between grippers 34. It is understood that in use the portion of uterus 166 nearer pivot pin 72 is the fundus 170 of uterus (that portion of uterus 166 which is opposite or remote from the opening of the uterus 166, the opening of uterus 166 not being shown in FIG. 4) and that lower uterine segment 168 of uterus 166 is nearer grippers 34 (the opening of uterus 166 can be to the left of grippers 34 in FIG. 4). To tighten belt 36 around uterus 166 (and thereby to compress uterus 166 more), the end of belt 36 opposite stop 162 is pulled toward handle 22 and then belt 36 is seated onto pins 126 using belt holes 142 which are closer to stop 162.

Regarding one option for assembling clamp 20, drill and crosspin post 24 with cross pin 48. Fuse weld cross pin 48 relative to post 24 and/or projection 42 of handle 22, and polish flush cross pin 48 relative to post 24. Insert the resultant assembly into base 60 of lower arm assembly 26, base 60 and lower rod 62 already having been attached together. Insert release lever 28 and torsion spring 30. Clip arms 118, 120 of torsion spring 30 to length. Pin using two pins 56; laser weld pins 56 relative to base 60, and polish flush. Insert the already assembled upper rod 124 and upper base 76 of upper arm assembly 32 into the resultant assembly. Insert pivot pin 72; laser weld both sides of pivot pin 72 relative to base 60 of lower arm assembly 26, and polish flush. Attach tip sub-assembly 128 of upper arm assembly 32 to upper rod 124; properly locate and orient; TIG weld all around the connection between this tip sub-assembly 128 and upper rod 124; and polish this weldment. Attach tip sub-assembly 64 of lower arm assembly 26 to lower rod 62; properly locate and orient; TIG weld all around the connection between this tip sub-assembly 64 and lower rod 62; and polish this weldment. Slidably insert a respective gripper 34 into each of tips 86, 146 and position in T-slots 102, 156. When forming the parts of clamp 20, all burrs and sharp edges should be removed unless otherwise specified. Clamp 20 must operate smoothly when assembled. All parts of clamp 20 (except possibly belt 36 and grippers 34) can be made of a metal. Parts can be passivated during assembly at appropriate times. Alternatively, all parts of clamp 20 can be assembled together but for grippers 34, belt 36, handle 22, and cross pin 48. This sub-assembly can be passivated as a unit (such passivation can occur, for example, using a bath). Then, handle 22 can be attached to post 24 using cross pin 48, and cross pin 48 can be laser welded in place, as discussed above; this weldment can be wipe passivated. Further, to the extent that any laser etching is performed after such a main passivation step (for example, to provide such information as the lot code, a drawing number, a logo), the parts laser etched can be wipe passivated after such etching. Any or all of the materials of clamp 20 can be biologically inert and corrosion resistant.

In use, clamp 20 can be used relative to a Caesarean section delivery of a baby, such as a human baby. As indicated above, clamp 20 can be used to prevent life-threatening bleeding following delivery of the baby by applying pressure to the uterus 166. Optionally, clamp 20 can be used to retract uterus 166 from the pelvis of the patient, for example, following the delivery of the baby via the Caesarean section delivery. Alternatively, uterus 166 can be retracted from pelvis and essentially laid on the abdomen of the patient by way of the hands of the operating room personnel (and thus not by way of clamp 20). Belt 36 is threaded first through lower slot 100 (in a distal to a proximal direction) and then through upper slot 154 (in a proximal to distal direction). Stop 162 prevents belt 36 from being pulled all of the way through lower tip 86. Grippers 34 are selectively opened and closed using release lever 28 and upper projection 134 of upper arm assembly 32. Clamp 20 is positioned about uterus 166 with belt 36 positioned in slots 100, 154 and proceeding circumferentially around uterus 166 at or near fundus 170 of uterus 166. Optionally, grippers 34 can be clamped to the lower uterine segment 168; the clamping of grippers 34 can be positioned upward (that is, toward fundus 170 and away from the natural opening (not shown) of uterus 166) from the transverse uterine incision (indicated by point 178 in FIG. 4) used to remove the baby and the placenta from uterus 166 (further, to the extent that an additional incision is used to release the water, then grippers 34 can be similarly placed upward relative to this incision). Release lever 28 is secured to the grooves between teeth 116. Belt 36 can be tightened to provide the desired degree of compression of belt 36 on uterus 166. Belt 36 is secured to pins 126 through belt holes 142. Optionally, clamp 20 can be oriented anterior and inferior towards the bladder. Lower rod 62 can be oriented generally adjacent the patient's body, while upper rod 124 is oriented generally away from the patient's body. Further, grippers can be generally directed inferior relative to patient's body. Clamp 20 can be clamped onto uterus during the procedure, such as when suturing the transverse uterine incision and generally preparing the uterus to be positioned back in the patient's body. Grippers 34 can be clamped onto lower uterine segment so as to pinch blood flowing in uterus, such as arterial blood flow, and thereby to have minimal blood flow in uterus. By way of example and not by way of limitation, grippers 34 can be clamped in place for approximately 10-30 seconds. Further, belt 36 can be initially secured in place relative to pins 126 to provide a desired amount of compression about uterus (initially, this amount of compression could be little to no compression, depending upon the circumstances). If uterus 166 is not found to contract, then belt 36 can be tightened to provide additional compressive forces to uterus 166. The transverse uterine incision 178 can then be sutured. Again, if uterus 166 is not contracting to a sufficient degree, belt 36 can be tightened even further. To remove clamp 20 from uterus 166, release lever 28 can be depressed to release release lever 28 from the grooves between teeth 116. Proximal projection 130 of upper arm assembly 32 can be moved away from handle 22 to separate grippers 34 from one another and to thereby release the hold on uterus 166. Further, belt 36 can be pulled off of pins 126 to loosen belt 36 around uterus 166.

Figure 12:
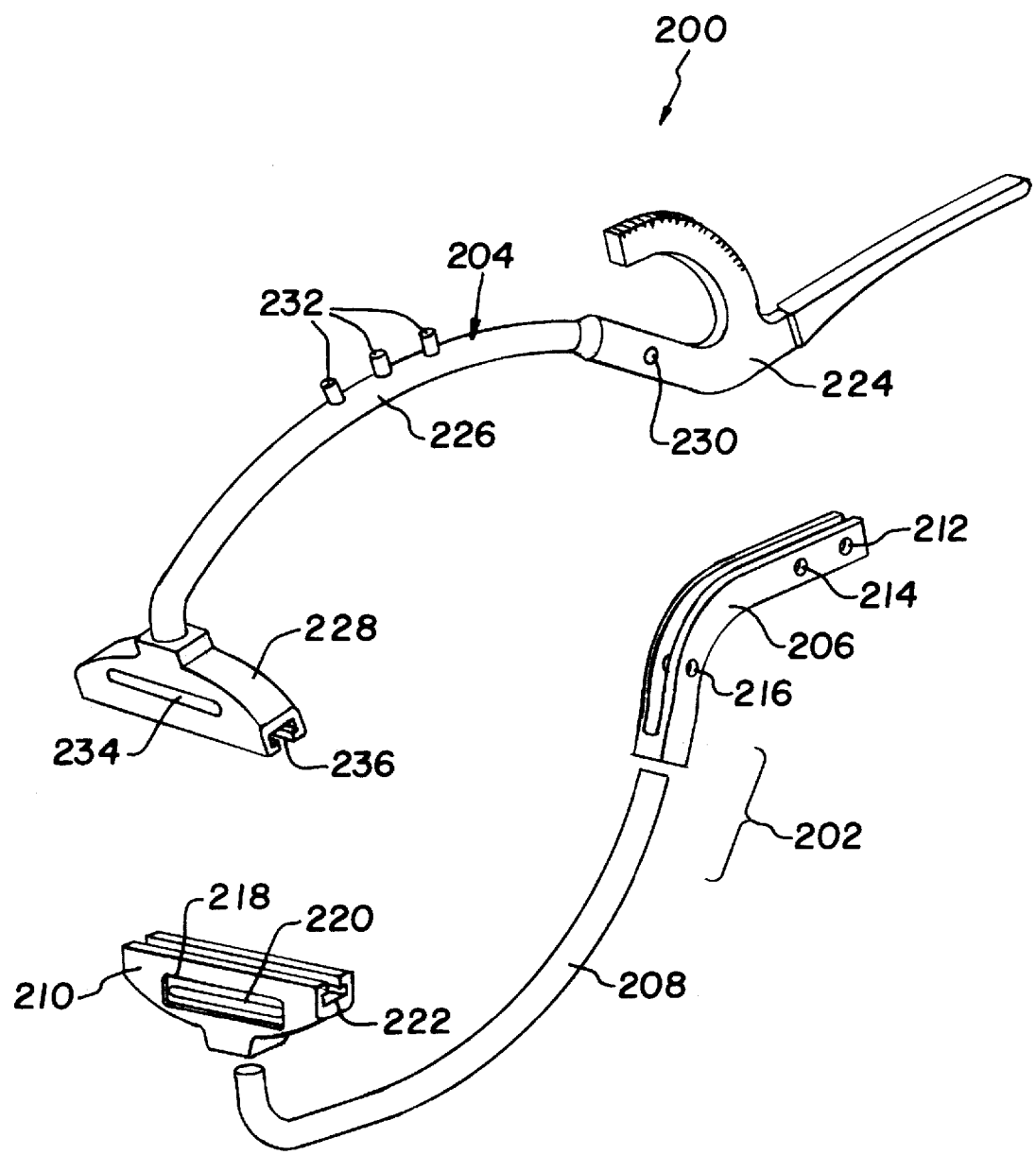
FIG. 12 is a partially exploded, perspective view of another embodiment of the uterine compression clamp according to the present invention, with certain parts being broken away.

FIG. 12 shows an alternative embodiment of the uterine compression clamp of the present invention. This clamp has the reference number 200. Clamp 200 functions in principle like clamp 20 and includes parts having substantially similar geometry as clamp 20, except as shown in FIG. 12. Thus, several parts are omitted from FIG. 12. Further, clamp 200 can be made of substantially similar material and in substantially similar ways as clamp 20. FIG. 12 shows lower arm assembly 202 and upper arm assembly 204 of clamp 200, assemblies 202, 204 being exploded from one another. Further, certain parts of lower arm assembly 202 are shown exploded from each other. Lower arm assembly 202 includes lower base 206, lower rod 208, and lower tip 210. Lower base 206 includes opposing holes 212 for receiving a pin for securing a post, opposing holes 214 for receiving a pin for securing a torsion spring and a release lever, and opposing holes 216 for receiving a pivot pin to pivotally couple lower and upper arm assemblies 202, 204 together. Lower rod 208 directly connects to lower tip 210. Lower rod 208 can conceivably be TIG welded to a blind hole of lower tip 210, and an appropriate filler and a polish blend can be used relative to this TIG weldment; alternatively, lower rod 208 can be attached to lower tip 210 using a cross pin arrangement and laser welding as described relative to clamp 20. Lower tip 201 includes a channel 218, a slot 220 for receiving a belt, and a T-slot 222 for receiving a gripper. Upper arm assembly 204 includes an upper base 224, an upper rod 226, and an upper tip 228. Upper base 224 includes a through-hole 230 for receiving the pivot pin, as well as additional features similar to clamp 20. Upper rod 226 receives a plurality of pins 232 for connecting to the belt. Upper rod 226 directly connects to upper tip 228. Upper rod 226 can conceivably be TIG welded to a blind hole of upper tip 228, and an appropriate filler and a polish blend can be used relative to this TIG weldment; alternatively, upper rod 226 can be attached to upper tip 228 using a cross pin arrangement and laser welding as described relative to clamp 20. Upper tip 228 includes a slot 234 for receiving the belt, and a T-slot 236 for receiving a gripper.

The present invention further provides a method of using a medical clamp 20. The method includes the steps of: providing lower arm assembly 26 and upper arm assembly 32; connecting pivotally upper arm assembly 32 to lower arm assembly 26; connecting belt 36 to lower arm assembly 26 and upper arm assembly 32; forming a loop 160, using belt 36, between lower arm assembly 26 and upper arm assembly 32; and clamping lower arm assembly 26 and upper arm assembly 32 relative to one another. Lower arm assembly 26 includes a longitudinally extending lower rod 62 and a lower tip 86 which is coupled with and extends transversely relative to lower rod 62, upper arm assembly 26 including a longitudinally extending upper rod 124 and an upper tip 146 which is coupled with and extends transversely relative to upper rod 124. Lower tip 86 includes a proximal face 96, a distal face 94 including a channel 98, and a lower slot 100 extending from proximal face 96 of lower tip 86 to said channel 98 of distal face 94 of lower tip 86. Upper tip 146 includes a proximal face 152, a distal face 150, and an upper slot 154 extending from proximal face 152 of upper tip 146 to distal face 150 of upper tip 146. Lower arm assembly 26 includes a lower gripper 34 attached to lower tip 86 and upper arm assembly 32 includes an upper gripper 34 attached to upper tip 146, the method further including clamping a lower uterine segment 168 between upper gripper 34 and lower gripper 34. Belt 36 includes a stop 162 and a body 164 with a plurality of holes 142. The method further includes positioning stop 162 adjacent channel 98 and extending body 164 through lower slot 100 and upper slot 154. Upper rod 124 includes a plurality of pins 126 projecting therefrom, the method further including attaching selectively plurality of holes 142 to plurality of pins 126 and thereby adjusting a size of loop 160, and compressing, using loop 160, a portion (for example, a fundus 170) of a uterus 166. The alternative embodiment of FIG. 12 can be used in a similar manner.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical clamp, comprising:
   a lower arm assembly including a proximal end, a distal end, and a proximal face which faces said proximal end, said lower arm assembly including a longitudinally extending lower rod and a lower tip which is coupled with and extends transversely relative to said lower rod, said lower tip including said proximal face, a distal face including a channel, and a lower slot extending from said proximal face of said lower tip to said channel of said distal face of said lower tip, said lower arm assembly including a lower gripper attached to said lower tip;
   an upper arm assembly pivotally connected to said lower arm assembly, said lower arm assembly and said upper arm assembly configured for clamping relative to one another, said upper arm assembly including a longitudinally extending upper rod and an upper tip which is coupled with and extends transversely relative to said upper rod, said upper tip including a proximal face, a distal face, and an upper slot extending from said proximal face of said upper tip to said distal face of said upper tip, said upper arm assembly including an upper gripper attached to said upper tip, said upper gripper and said lower gripper being configured for clamping therebetween a lower uterine segment; and
   a belt connected to said lower arm assembly and said upper arm assembly and configured for forming a loop therebetween, said belt extending longitudinally from said proximal face, said belt including a stop and a body with a plurality of holes, said stop being positioned adjacent said channel, said body extending through said lower slot and said upper slot.

2. The medical clamp of claim 1, wherein said upper rod includes a plurality of pins projecting therefrom, said plurality of holes configured for being selectively attached to said plurality of pins and thereby for adjusting a size of said loop, said loop configured for compressing a portion of a uterus.

3. A method of using a medical clamp, said method comprising the steps of:
   providing a lower arm assembly and an upper arm assembly, said lower arm assembly including a proximal end, a distal end, and a proximal face which faces said proximal end, said lower arm assembly including a longitudinally extending lower rod and a lower tip which is coupled with and extends transversely relative to said lower rod, said lower tip including said proximal face, a distal face including a channel, and a lower slot extending from said proximal face of said lower tip to said channel of said distal face of said lower tip, said lower arm assembly includes a lower gripper attached to said lower tip, said upper arm assembly including a longitudinally extending upper rod and an upper tip which is coupled with and extends transversely relative to said upper rod, said upper tip including a proximal face, a distal face, and an upper slot extending from said proximal face of said upper tip to said distal face of said upper tip, said upper arm assembly includes an upper gripper attached to said upper tip;
   connecting pivotally said upper arm assembly to said lower arm assembly;
   connecting a belt to said lower arm assembly and said upper arm assembly, said belt extending longitudinally from said proximal face, said belt including a stop and a body with a plurality of holes;
   forming a loop, using said belt, between said lower arm assembly and said upper arm assembly; and
   clamping said lower arm assembly and said upper arm assembly relative to one another;
   positioning said stop adjacent said channel and extending said body through said lower slot and said upper slot; and
   clamping a lower uterine segment between said upper gripper and said lower gripper.

4. The method of claim 3, wherein said upper rod includes a plurality of pins projecting therefrom, the method further including attaching selectively said plurality of holes to said plurality of pins and thereby adjusting a size of said loop, and compressing, using said loop, a portion of a uterus.

\* \* \* \* \*